United States Patent [19]

Nakamura et al.

[11] Patent Number: 4,966,153
[45] Date of Patent: Oct. 30, 1990

[54] ULTRASONIC DOPPLER BLOOD FLOW VELOCITY DETECTION APPARATUS AND A METHOD FOR DETECTING BLOOD FLOW VELOCITY

[75] Inventors: Yasuhiro Nakamura, Tokyo; Ikuo Sakai, Kawasaki; Masami Kawabuchi, Yokohama, all of Japan

[73] Assignee: Matsushita Electric Industrial Co., Ltd., Osaka, Japan

[21] Appl. No.: 341,506

[22] Filed: Apr. 21, 1989

[30] Foreign Application Priority Data

Apr. 22, 1988 [JP] Japan ................................. 63-100739

[51] Int. Cl.$^5$ .............................................. A61B 8/06
[52] U.S. Cl. ............................. 128/661.09; 73/861.25
[58] Field of Search ................. 128/661.09; 73/861.25

[56] References Cited

U.S. PATENT DOCUMENTS 4,534,357  8/1985  Powers ............................ 128/661.09
4,751,847  6/1988  Katakura et al. .......... 128/661.09 R
4,780,837 10/1988  Namekawa ................ 128/661.09 R

FOREIGN PATENT DOCUMENTS 2541713  3/1977  Fed. Rep. of Germany .

Primary Examiner—Francis Jaworski
Attorney, Agent, or Firm—VandeSande & Priddy Pollock

[57] ABSTRACT

An ultrasonic Doppler blood flow velocity detection apparatus comprises: a pulse generation circuit for generating pulses at a predetermined interval; a transducer for transmitting ultrasonic waves in response to each of the pulses and for receiving reflected ultrasonic waves from a reflective object in the blood of a human body and converting the received ultrasonic waves into an electric echo signal; an extraction circuit for extracting signal components of first and second frequencies f1 and f2; a signal producing circuit for producing a signal having a frequency of $|f1-f2|$ using output signals of the extraction circuit; a detection circuit for detecting amplitude of an output signal of the frequency difference signal producing circuit circuit and for phase-comparing the output signal with a reference signal; and a reference signal generation circuit for generating the reference signal of a predetermined frequency fr in response to each of the pulses, the predetermined frequency fr being approximately equal to the frequency difference $|f1-f2|$. The invention also discloses a method for detecting blood flow velocity.

9 Claims, 4 Drawing Sheets

ULTRASONIC DOPPLER BLOOD FLOW VELOCITY DETECTION APPARATUS AND A METHOD FOR DETECTING BLOOD FLOW VELOCITY

BACKGROUND OF THE INVENTION

1. Field of the Invention:

This invention relates to an ultrasonic Doppler blood flow velocity detection apparatus and to a method for detecting blood flow velocity.

2. Description of the Prior Art:

An ultrasonic Doppler blood flow velocity detection apparatus is used for detecting blood flow velocity which can be used in diagnoses. There are many types of Doppler blood flow detection apparatus utilizing the Doppler effect through reflection of ultrasonic waves. The ultrasonic Doppler blood flow velocity detector can select a portion where blood flow is to be detected with respect to distance and direction.

The most popular Doppler blood flow velocity detection apparatus detects blood flow velocity as follows:

The Doppler blood flow velocity detection apparatus transmits an ultrasonic-wave pulse whose center frequency is "f", at a predetermined interval into the human body by a transducer; then it receives a reflected signal, i.e., an echo signal, from a moving reflective object, such as a blood corpuscle; and detects the amount of phase shift of the echo signal, i.e., Doppler shift. An output signal of the phase shift amount, i.e. Doppler signal, indicates blood flow velocity.

In the Doppler blood flow velocity detection apparatus, the relation between a shift frequency fd of a Doppler signal and blood flow velocity V is given by:

$$fd = (2V/c) \cdot f \cos \theta \quad (1)$$

where "c" is a sound velocity in the human body; $\theta$ is an angle made by the ultrasonic transmitting direction with the direction of blood flow, wherein the shift frequency fd is subjected to a limitation given by:

$$|fd| \leq fp/2 \quad (2)$$

where fp is a repetition frequency of ultrasonic-wave pulse (also referred to as a rate frequency). The Doppler shift frequency fd should not exceed a half of the frequency fp because of the sampling theory. If blood velocity V exceeds a velocity corresponding to ultrasonic-wave pulse repetition frequency fp, the ultrasonic Doppler blood flow velocity detection apparatus outputs incorrect velocity and direction. Particularly, if a deep portion is measured, the period of time from transmission of an ultrasonic-wave pulse to reception of the reflected ultrasonic waves by a sensor of the apparatus becomes long. Then, the frequency fp of the ultrasonic-wave pulse should be set to a low value. Therefore, it is difficult to detect a high velocity of blood flow.

An ultrasonic Doppler blood velocity detecting method is disclosed in the technical report of the Institute of Electronics, Information and Communication Engineers, Vol. 87, No. 294, U.S. 87-51, 1987, which is provided to moderate the limitation of measurable blood flow velocity.

FIG. 6 shows a waveform of transmitted ultrasonic-wave pulses according to the above-mentioned prior art. In FIG. 6, ultrasonic-wave pulses are outputted repeatedly at intervals T and T+Ts alternately. The echo signal has phase shift $\Delta\theta$ when an ultrasonic-wave pulse is transmitted which has the interval T to the subsequent pulse and phase shift $\Delta\theta'$ when an ultrasonic-wave pulse is transmitted which has the interval Ts to the subsequent pulse. A velocity of blood flow is given by a phase shift $\Delta\Delta\theta$ which is obtained by $\Delta\theta'-\Delta\theta$. The measurable range is given by $$|fd| \leq (\tfrac{1}{2}) \cdot (1/Ts);$$

Therefore, decrease in Ts extends measurable range of blood flow velocity in consideration of Equation (1).

However, there is a drawback that the ultrasonic Doppler blood velocity detection apparatus according to the above-mentioned method is complicated because ultrasonic-wave pulses should be transmitted at two different intervals and a phase shift calculation is required to obtain the phase shift $\Delta\Delta\theta$. The detection of the phase shift $\Delta\Delta\theta$ should be measured repeatedly to obtain a means value because it is not accurate. Therefore, there is also a drawback that it is impossible to obtain an instantaneous value of the blood flow velocity.

SUMMARY OF THE INVENTION

The present invention has been developed in order to remove the above-described drawbacks inherent to the conventional ultrasonic Doppler blood flow velocity detection apparatus.

According to the present invention there is provided an ultrasonic Doppler blood flow velocity detection apparatus comprising: a pulse generation circuit for generating pulses at a predetermined interval; a transducer for transmitting ultrasonic waves in response to each of said pulses and for receiving reflected ultrasonic waves from an ultrasonic-wave reflective object in the blood of a human body and converting the received ultrasonic waves into an electric echo signal; a first signal extraction circuit for extracting signal component of a first frequency f1 from said echo signal; a second signal extraction circuit for extracting a signal component of a second frequency f2 different from said first frequency f1 from said echo signal; a frequency difference signal producing circuit for producing a signal having a frequency of $|f1-f2|$ using output signals of said first and second signal extracting circuit; a detection circuit for detecting amplitude of an output signal of said frequency difference signal producing circuit and for phase-comparing said output signal with a reference signal; and a reference signal generation circuit for generating said reference signal of a predetermined frequency fr in response to each of said pulses, said predetermined frequency fr being approximately equal to the frequency difference $|f1-f2|$.

According to the present invention there is also provided a method for an ultrasonic Doppler blood flow velocity detection comprising the steps of: generating pulses at a predetermined interval; transmitting ultrasonic waves in response to each of said pulses and receiving the reflected ultrasonic waves from an ultrasonic-wave reflective object in the blood of a human body and converting the received ultrasonic waves into an electric echo signal; extracting a signal component of a first frequency f1 from said echo signal; extracting a signal component of a second frequency f2 different from said first frequency f1 from said echo signal; producing a signal having a frequency $|f1-f2|$ using output signals of said first and second signal extracting steps; detecting amplitude of an output signal of said producing step and phase-comparing said output signal with said reference signal; and generating a reference signal of a predetermined frequency fr in response to each of the pulses, said predetermined frequency fr being approximately equal to the frequency difference $|f1-f2|$.

BRIEF DESCRIPTION OF THE DRAWINGS

The object and features of the present invention will become more readily apparent from the following detailed description taken in conjunction with the accompanying drawings in which.

The same or corresponding elements or parts are designated at like references throughout the drawings.

DETAILED DESCRIPTION OF THE INVENTION

Figure 1:
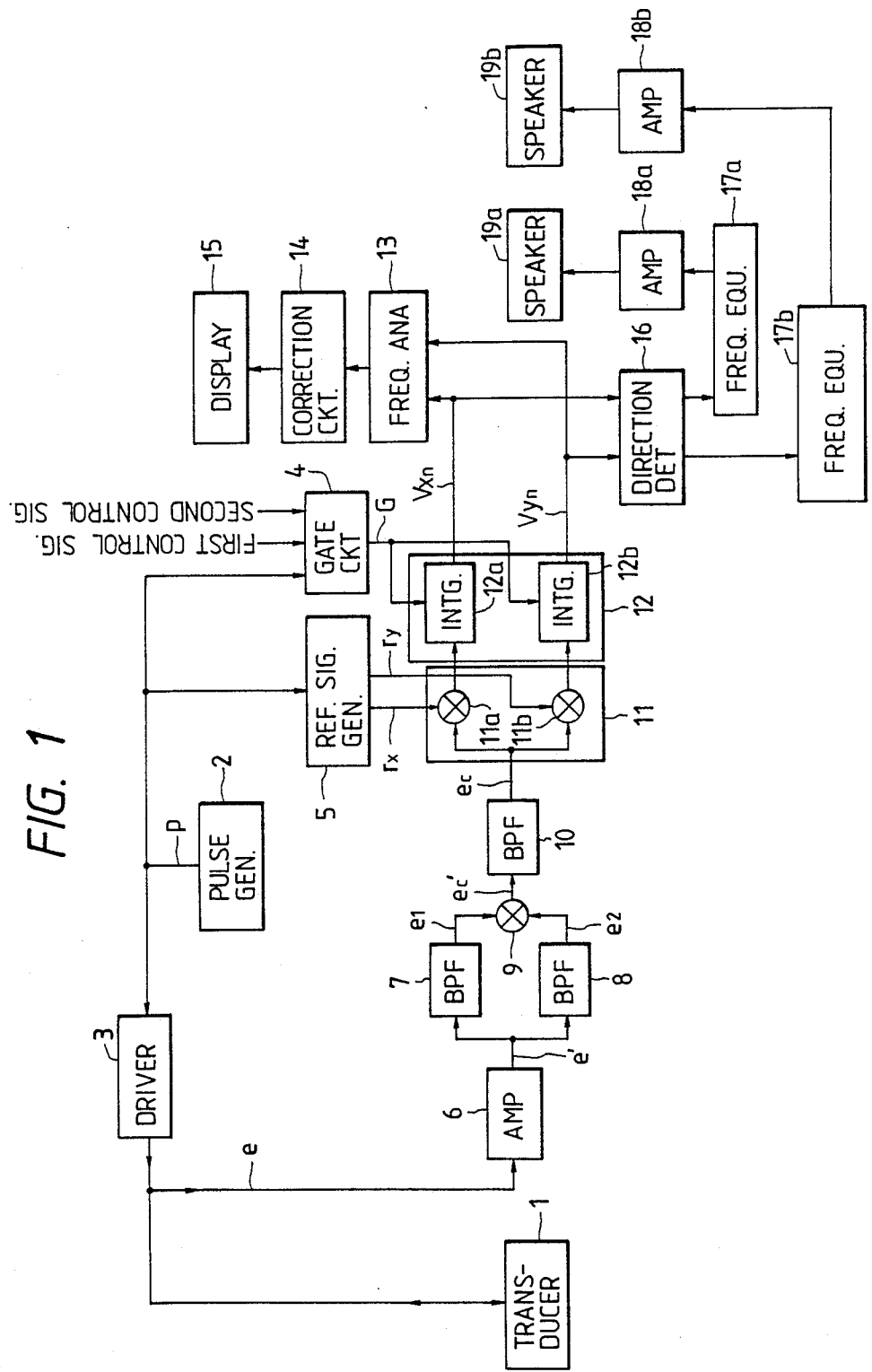
FIG. 1 is a block diagram of an ultrasonic Doppler blood flow velocity detection apparatus according to the invention.

Referring now to the drawings, FIG. 1 is a block diagram of an ultrasonic Doppler blood flow velocity detection apparatus of the invention.

Figure 2:
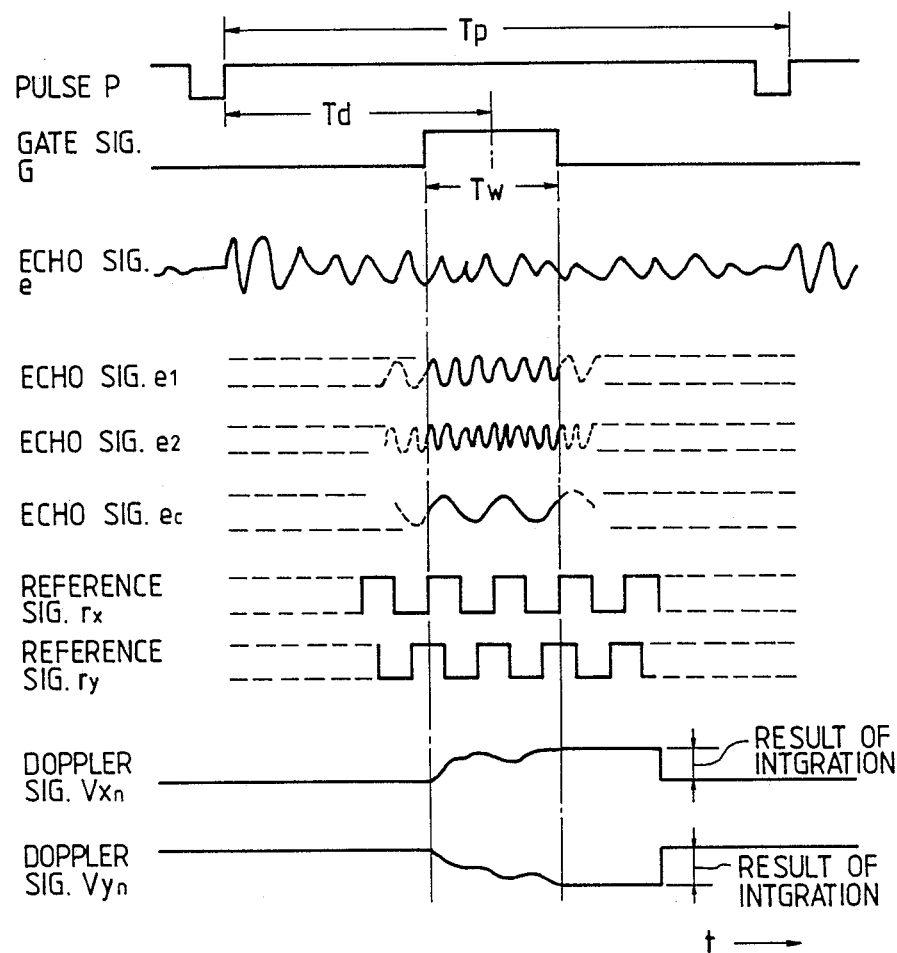
FIG. 2 shows waveforms for illustrating the operation of the ultrasonic Doppler blood flow velocity detection apparatus of FIG. 1.

In FIG. 1, a pulse generator 2 produces a pulse signal P at a predetermined interval Tp shown in FIG. 2. A driver 3 produces an ultrasonic drive signal in response to an output signal of the pulse generator 2. The transducer 1 outputs an ultrasonic-wave signal in response to the ultrasonic drive signal. The ultrasonic-wave signal transmitted from the transducer 1 is reflected at an object, such as a blood corpuscle in the blood. The reflected ultrasonic-wave signal is received by the transducer 1. The transducer 1 converts the reflected and received ultrasonic-wave signal into an electric signal which will be referred to as an echo signal "e". The echo signal "e" is sent to an amplifier 6 which amplifies the echo signal "e" at a predetermined gain in order to obtain a desired output level. An output signal of the amplifier 6 is sent to a first bandpass filter 7 whose center frequency is $f_1$ and to a bandpass filter 8 whose center frequency is $f_2$ which is different from $f_1$. The first and second bandpass filters 7 and 8 extract frequency components of $f_1$ and $f_2$ respectively. A multiplier 9 multiplies an echo signal $e_1$ of an output signal from the first bandpass filter 7 by an echo signal $e_2$ of an output signal from the second bandpass filter 8 and outputs a product echo signal $e'_0$. A third bandpass filter 10 extracts a component of a frequency $f_0$ from the produce echo signal $e'_0$ to product and output an echo signal $e_0$. The echo signal $e_0$ or the output signal of the third bandpass filter 10 is sent to a detector 11 (also referred to as a quadrature detector) which has two multipliers 11a and 11b. The multiplier 11a multiplies the echo signal $e_0$ by a reference signal $r_x$ which is produced by a reference signal generator 5, and whose frequency substantially equals the frequency $f_0$ of bandpass center frequency of the bandpass filter 10. The multiplier 11b multiplies the echo signal $e_0$ by a reference signal $r_y$ which is produced by a reference signal generator 5, and whose frequency substantially equals the frequency $f_0$ of the center frequency of the bandpass filter 10. The reference signal generator 5 produces the reference signals $r_x$ and $r_y$ (also referred to as quadrature reference signals), in response to the output signal of the pulse generator 2, which have a phase difference of 90° to each other. The output signals of multipliers 11a and 11b are used for detecting direction of the movement of the object. Output signals of the multipliers 11a and 11b are sent to integrators 12a and 12b respectively which integrate the output signals in response to an output signal of a gate circuit 4. The gate circuit 4 produces a gate signal G in response to the pulse signal P with delay time Td shown in FIG. 2. The delay time Td is determined by a first control signal applied to the gate circuit 4. The gate signal G has a duration Tw which is determined by a second control signal applied to the gate circuit 4. The delay time Td determines the center of the duration of the gate signal Td, as shown in FIG. 2. The integrators 12a and 12b integrate output signals from the multipliers 11a and 11b respectively in response to the gate signal G for a duration Tw to output Doppler signals $V_{xn}$ and $V_{yn}$ respectively.

The detector 11 detects a blood flow velocity from the echo signal $e_0$ in response to the reference signals $r_x$ and $r_y$. The integrators 12a and 12b respectively integrate the output signals of the quadrature detector 11 in response to the gate signal with the delay time Td indicative of the depth of a portion where blood flow velocity is measured, for the duration of time Tw indicative of a region to be measured.

The Doppler signals Vxn and Vyn are sent to a frequency analyzer 13 which analyzes the Doppler signal $V_{xn}$ and $V_{yn}$ to output a spectrum signal indicative of level of plural frequency components. A correction circuit 14 corrects levels of plural frequency components of the spectrum signal. A display 15 displays blood flow velocity information repeatedly according to the output signal of the correction circuit.

The Doppler signals $V_{xn}$ and $V_{yn}$ may be processed by the following circuits. A direction detector 16 detects the direction of blood flow in response to the Doppler signals $V_{xn}$ and $V_{yn}$ as to whether the object moves "toward" or "away" from the transducer 1. In this specification, the term "toward" is used to indicate the direction of the object moving toward the transducer 1; the term "away", to indicate the direction of the object moving away from the transducer 1. The direction detector 16 outputs either of Doppler signals $V_{xn}$ and $V_{yn}$. Frequency equalizers 17a and 17b equalize output signals of the direction detector 16 for compensating for frequency characteristic of the Doppler signals $V_{xn}$ and $V_{yn}$ respectively. Amplifiers 18a and 18b amplify output signals of the frequency equalizers 17a and 17b to drive speakers 19a and 19b respectively. Speakers 19a and 19b emit sounds in response to the output signals of the amplifiers 18a and 18b respectively to inform an operator of the Doppler signals indicative of blood flow velocity to an operator, such as stereo reproduction.

Hereinbelow will be described operation of the ultrasonic Doppler blood flow velocity detection apparatus.

The received ultrasonic-wave signal, i.e., echo signal "e" is applied to the bandpass filters 7 and 8. The bandpass filters 7 and 8 have center frequencies $f_1$ and $f_2$ respectively. The frequency difference between the center frequencies $f_1$ and $f_2$ is set to $f_0$. The echo signal "e" is subjected to phase shift by the movement of the object which reflects transmitted ultrasonic-wave signal, the Doppler effect. Therefore, the echo signal "e" has a spectrum distribution according to the phase shift. The echo signal "e" is processed as it passes through bandpass filters 7 and 8 having different pass bands. In this way two echo signals $e_1$ and $e_2$ having different center frequencies $f_1$ and $f_2$ are obtained. The multiplier 9 produces the product echo signal $e'_0$ of a beat signal between echo signals $e_1$ and $e_2$ by multiplying the echo signal $e_1$ by the echo signal $e_2$. The bandpass filter 10 is set to have a center frequency $f_0$ which is equal to the frequency difference between the center frequencies of the bandpass filters 7 and 8, and which is approximately equal to the frequency of the reference signals $r_x$ and $r_y$. Thus, a signal component of frequency $f_0$ is extracted from the product echo signal $e'_0$ by the bandpass filter 10. The multipliers 11a and 11b multiply the echo signal $e_0$ by the reference signals $r_x$ and $r_y$ to provide detection signals indicative of amplitude and phase relation between the echo signal $e_0$ and the reference signals $r_x$ and $r_y$ respectively. If the echo signal $e_0$ is in phase with the reference signal $r_x$ the output level of the multiplier 11a is large. If the echo signal $e_0$ has a phase displacement of 90° with the reference signal $r_x$ the output level of the multiplier is small. Similarly, if the echo signal $e_0$ is in phase with the reference signal $r_x$, the output level of the multiplier 11a is large. If the echo signal $e_0$ has a phase displacement of 90° with the reference signal $r_x$ the output level of the multiplier is small.

Hereinbelow will be described operation of the ultrasonic Doppler blood flow detection apparatus more specifically.

The received echo signal $e_1$ has a spectrum distribution because of the Doppler effect. The echo signals $e_1$ and $e_2$ are given by:

$$e_1 = A_1 \cdot \sin\{\omega_1(t+\Delta t_n)\}$$

$$e_2 = A_2 \cdot \sin\{\omega_2(t+\Delta t_n)\}$$

$$(\omega_1 = 2\pi f_1, \omega_2 = 2\pi f_2) \quad (5)$$

where A1 and A2 are amplitudes; $\omega_1$ and $\omega_2$ are angular frequencies corresponding to the center frequencies $f_1$ and $f_2$ of the bandpass filters 7 and 8 respectively; and $\Delta t_n$ is a difference between periods of time required for receiving the reflected echo signal at $(n-1)'^{th}$ detection and that at $n'^{th}$ detection. This difference corresponds to a distance of movement of the reflective object. If the reflective object moves, $\Delta t$ varies because a period of time for transmission from the reflective object to the transducer 1 changes.

The product echo signal $e'_0$ which is outputted at the multiplier 9 is given by $$e'_0 = (\tfrac{1}{2})A_1A_2[\cos\{(\omega_1-\omega_2)(t-\Delta t_n)\} - \cos\{(\omega_1+\omega_2)(t+\Delta t_n)\}] \quad (6)$$

which has frequency components of sum of $\omega_1$ and $\omega_2$ and difference between $\omega_1$ and $\omega_2$. Therefore, the echo signal $e_0$ is given by:

$$e_0 = (\tfrac{1}{2}) \cdot A_1 A_2 \cos\{\omega_0(t-\Delta t_n)\} \quad (7)$$

This is done by passing the product echo signal $e'_0$ through the bandpass filter 10. It is assumed that $A_1 = A_2 (=A)$ because the echo signals $e_1$ and $e_2$ are detected at the same point. Thus, the echo signal $e_0$ is given by:

$$e_0 = (\tfrac{1}{2})A^2 \cos\{\omega_0(t-\Delta t_n)\} \quad (8)$$

The reference signals $r_x$ and $r_y$ are:

$$r_x = 1 \cdot \cos \omega_r t$$

$$r_y = 1 \cdot \sin \omega_r t \quad (9)$$

where "1" is an amplitude; and $\omega_r = 2\pi f_r$.

The Doppler signals $V_{xn}$ and $V_{yn}$ are obtained by multiplying the echo signal $e_0$ by the reference signals $r_x$ and $r_y$ and by integration by the integrators 12a and 12b. The frequencies of the reference signals $r_x$ and $r_y$, the difference frequency between center frequencies of the bandpass filters 7 and 8, and the center frequency of the bandpass filter 10 are set to be the same value, i.e., $f_0$. Therefore, the Doppler signals $V_{xn}$ and $V_{yn}$ are given by:

$$V_{xn} = e_0 r_x$$
$$= (\tfrac{1}{2})A^2 \cos(\omega_0 \Delta t_n)$$
$$V_{yn} = e_0 r_y$$
$$= (\tfrac{1}{2})A^2 \sin(\omega_0 \Delta t_n) \quad (10)$$

The Doppler signals $V_{xn}$ and $V_{yn}$ which are obtained at $n'^{th}$ transmission and receiving are discrete signals and indicate a phase of the echo signal $e_0$ with the reference signals $r_x$ and $r_y$. It is assumed that $\Delta t_n$ is a variation of time period $\Delta t'_n$ per interval Tp for transmission and receiving the ultrasonic-wave signal. The Doppler signals $V_{xn}$ and $V_{yn}$ are given by:

$$V_{xn} = (\tfrac{1}{2})A^2 \cos(\omega_0 \Delta t'_n/T p)$$

$$V_{yn} = (\tfrac{1}{2})A^2 \sin(\omega_0 \Delta t'_n/T p) \quad (11)$$

Eq. (11) is given at a discrete time T by:

$$V_{xn} = (\tfrac{1}{2})A^2 \cos(\omega_d \cdot T)$$

$$V_{yn} = (\tfrac{1}{2})A^2 \sin(\omega_d \cdot T) \quad (12)$$

The relation between $\omega_d$ and $\omega_0$ is given by:

$$\omega_d = \omega_0(\Delta t'_n/T p) \quad (13)$$

The variation of time period is given by:

$$\Delta t'_n = (2/c)(\Delta l_n/T p) = (2/c)V \quad (14)$$

where $\Delta l_n/T p$ is a distance over which the reflective object moves, i.e., velocity V. From Eqs. (13) and (14), a Doppler shift frequency $f_d$ with respect to a velocity V is given by:

$$f_d = (2V/c)f_0 \cdot \cos\theta \quad (15)$$

The Doppler shift frequency $f_d$ is subjected to the same limitation as Eq. (2).

The frequency analyzer 13 provides the Doppler shift frequency $f_d$ by frequency analyzing of the Doppler signals $V_{xn}$ and $V_{yn}$. However, amplitudes of the Doppler signals $V_{xn}$ and $V_{yn}$ are not proportional to amplitude of the echo signal "e" because amplitudes of the Doppler signals $V_{xn}$ and $V_{yn}$ are given by a term $A^2$. The correction circuit 14 corrects the Doppler signals $V_{xn}$ and $V_{yn}$ so that the output signal is directly proportional to the amplitude of the receive echo signal.

The frequency $f_o$ determining the frequency of the Doppler shift signal $f_d$ has no relation to a frequency of the transmitted ultrasonic-wave signal but corresponds to the difference frequency between the center frequencies $f_1$ and $f_2$ of the bandpass filters 7 and 8 and to the reference frequency $f_r$. Therefore, the measurable range can be extended by selecting the value of the frequency $f_o$. For example, if the center frequency of the ultrasonic-wave signal is 5 MHz and the repetition frequency $f_p$ is 3 KHz, the ultrasonic Doppler blood flow velocity of up to about 230 cm/sec is measurable where the center frequency $f_1$ of the first bandpass filter is set to be 4.75 MHz; the center frequency of the second bandpass filter $f_2$, to be 5.25 MHz; and thus, the reference frequency $f_r$ is to be the frequency $f_0(=f_2-f_1=500$ KHz). On the other hand, in the above-mentioned prior art, the measurable velocity range is about 23 cm/sec from Eqs. (1) and (2) where C=1540 m/sec, $\theta=0$. Therefore, the measurable range of blood flow velocity of ultrasonic Doppler blood flow velocity detection according to the invention is ten times that of the prior art ultrasonic Doppler blood flow velocity detector.

Figure 3:
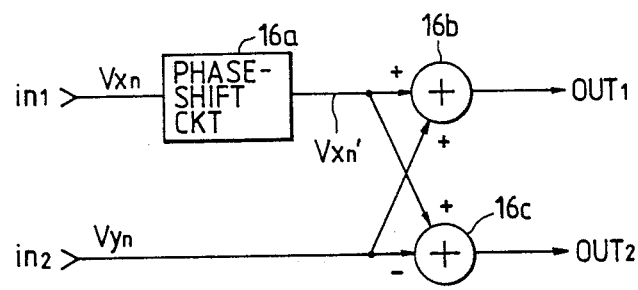
FIG. 3 is a block diagram of direction detector of FIG. 1.

Each of the Doppler signals $V_{xn}$ and $V_{yn}$ shows the blood flow velocity and it is determined by a relation between the Doppler signals $V_{xn}$ and $V_{yn}$ whether the object moves in the direction of "toward" or "away". FIG. 3 is a block diagram of the direction detector 16 which detects the direction of movement of the object in accordance with the relation between the Doppler signals $V_{xn}$ and $V_{yn}$. In FIG. 3, the Doppler signal $V_{xn}$ is applied to a phase-shift circuit 16a for phase-shifting it by 90° of the reference signals $r_x$. The Doppler signal $V_{yn}$ is added to the output signal of the phase-shift circuit 16a, shown by $V'_{xn}$ in the drawing, by an adder 16b. The signal $V'_{xn}$ is subtracted from the Doppler signal $V_{yn}$ by a subtractor 16c. Output signals of the adder 16b and subtractor 16c are sent to the equalizers 17a and 17b respectively.

It is assumed that a Doppler shift by "toward" flow of blood is $+d\omega$; another Doppler shift by "away" flow of blood, $-d\omega$. In the case of "toward" flow of blood, Eq. (12) is:

$$V_{xn}=(\tfrac{1}{4})A^2 \cos(+\omega_d\cdot T)=(\tfrac{1}{4})A^2 \cos(\omega_d\cdot T)$$

$$V_{yn}=(\tfrac{1}{4})A^2 \sin(\omega_d\cdot T)=(\tfrac{1}{4})A^2 \sin(\omega_d\cdot T) \quad (12a)$$

in the case of "away" flow of blood, Eq. (12) is:

$$V_{xn}=(\tfrac{1}{4})A^2 \cos(-\omega_d\cdot T)=(\tfrac{1}{4})A^2 \cos(\omega_d\cdot T)$$

$$V_{yn}=(\tfrac{1}{4})A^2 \sin(-\omega_d\cdot T)=(\tfrac{1}{4})A^2 \sin(\omega_d\cdot T) \quad (12b)$$

The phase-shift circuit 16a shifts the Doppler signal $V_{xn}$ by 90° to output the signal $V'_{xn}$. Therefore, at either outputs of the adder 16b and subtractor 16c, a Doppler signal is selectively outputted. The signal $V'_{xn}$ is:

$$V_{xn}=(\tfrac{1}{4})A^2 \sin(\omega_d+T) \quad (12c)$$

The output signal $V_{OUT1}$ of the adder 16a and the output signal $V_{OUT2}$ of the subtractor 16c are:

$$V_{OUT1}=V_{xn}'+V_{yn}$$

$$V_{OUT2}=V_{xn}'-V_{yn} \quad (12d)$$

In the case of "toward" flow of blood, $V_{OUT1}$ and $V_{OUT2}$ are:

$$V_{OUT1}=(\tfrac{1}{2})A^2 \sin(\omega_d\cdot T)$$

$$V_{OUT2}=0 \quad (12e)$$

In the case of "away" flow of blood, $$V_{OUT1}=0$$

$$V_{OUT2}=(\tfrac{1}{2})A^2 \sin(\omega_d\cdot T) \quad (12f)$$

Therefore, in the case of "toward" flow of blood, the Doppler signal is outputted from the output OUT1; in the case of "away" flow of blood, the Doppler signal is outputted from the output OUT2. Thus, either sound signals from the speakers 19a and 19b are outputted according to movement direction of the reflective object. The sound signals indicative of Doppler signals show the blood flow velocity well because the direction of blood flow is clearly indicated and sound signals are corrected to show linear characteristics.

Figure 4:
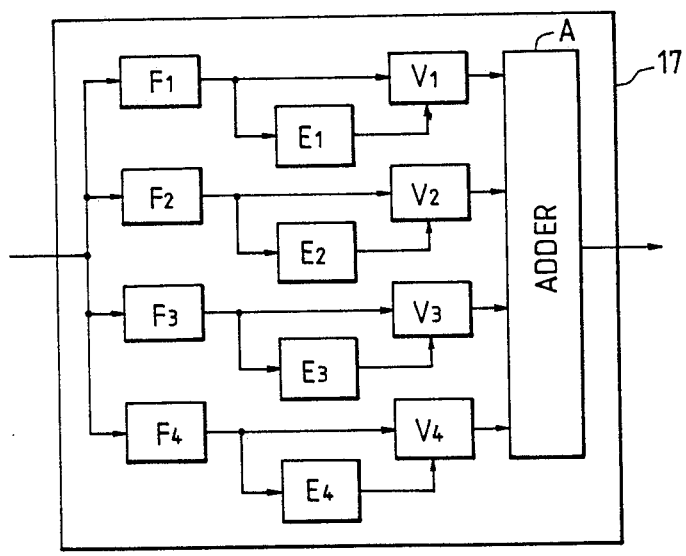
FIG. 4 is a block diagram of frequency equalizer of FIG. 1.
Figure 5:
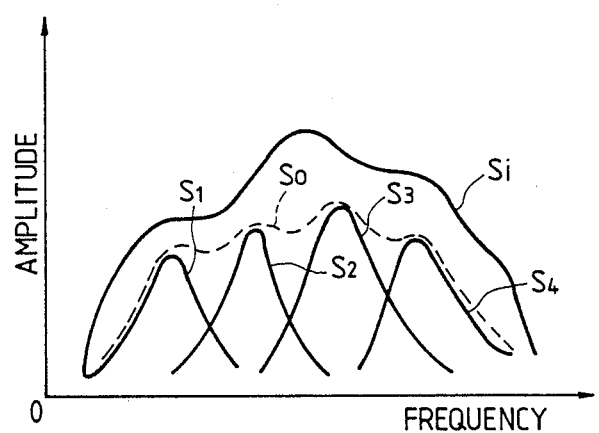
FIG. 5 is a chart for illustrating the operation of the frequency equalizer of FIG. 4.
Figure 6:
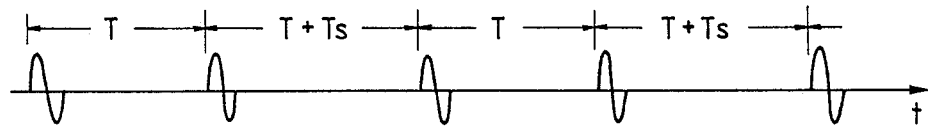
FIG. 6 shows a waveform of a prior art ultrasonic Doppler blood velocity detection apparatus and a method.

FIG. 4 shows a block diagram of frequency equalizer 17. In FIG. 4, the operator can judge the blood flow velocity by listening to sound signals indicative of the Doppler signals $V_{xn}$ and $V_{yn}$ and by recognizing its tone. However, a level of the sound signal is not directly proportional to that of received echo signal because the Doppler signals $V_{xn}$ and $V_{yn}$ have the term $A^2$, as shown in Eq. (12). The frequency equalizer 17 is provided for correcting this relation. The frequency equalizer 17 comprises four bandpass filters F1, F2, F3, and F4 having different bandpass characteristics, and whose inputs are connected, in common, to the output of the direction detector 16. The frequency equalizer 17 further includes amplitude detectors E1, E2, E3, and E4 for detecting amplitudes of outputs of the bandpass filters F1, F2, F3, and F4 respectively, Electronic volume control circuits V1, V2, V3, and V4 are included in equalizer 17 for amplifying output signals of bandpass filters F1, F2, F3, and F4 at gains determined by levels of signals from the amplitude detectors E1, E2, E3, and E4 respectively so that each gain is proportional to the square root of input level thereof. Equalizer 17 further includes adder for adding output signals of the electronic volume control circuits V1, V2, V3, and V4. The output signal of the detection circuit 16 is equalized with respect to the level over a frequency range by the frequency equalizer 17. Therefore, the sound signals from the speakers 19a and 19b have sound levels proportional to the level of the echo signal. FIG. 5 shows frequency characteristics for illustrating the equalizer 17. In FIG. 17, a curve "Si" shows frequency spectrum of the input signal of the equalizer 17; curves $S_1$ to $S_2$ show frequency spectrums of output signals of the electronic volume circuits V1, V2, V3, and V4; and a curve $S_0$ shows a frequency spectrum of the output signal of the equalizer 17.

As mentioned above, the ultrasonic Doppler blood flow velocity detection apparatus according to the invention can detect a high speed blood flow velocity by extracting two components of different frequencies from the echo signal; extracting a component of that difference frequency from these components; and by detecting a Doppler signal by multiplying the component by the quadrature reference signals of that difference frequency.

What is claimed is:

1. An ultrasonic Doppler blood flow velocity detection apparatus comprising:
    (a) transducing means for transmitting ultrasonic waves in response to each pulse of a pulse train and for receiving reflected ultrasonic waves from an ultrasonic-wave reflective object in the blood of a human body and converting the received ultrasonic waves into an electric echo signal;
    (b) first signal extraction means for extracting a signal component of a first frequency f1 from said echo signal by directly filtering said echo signal;
    (c) second signal extraction means for extracting a signal component of a second frequency f2 different from said first frequency f1 from said echo signal by directly filtering said echo signal;
    (d) frequency difference signal producing means for producing a signal having a frequency of $|f1-f2|$ using said signal components of said first and second signal extracting means;
    (e) detection means for detecting amplitude of an output signal of said frequency difference signal producing means and for phase-comparing said output signal with a reference signal; and
    (f) reference signal generation means for generating said reference signal of a predetermined frequency fr in response to each of said pulses, said predetermined frequency fr being approximately equal to the frequency difference $|f1-f2|$.

2. An ultrasonic Doppler blood flow velocity detection apparatus as claimed in claim 1, wherein said detection means is a first multiplier for multiplying an output from said frequency difference signal producing means by said reference signal.

3. An ultrasonic Doppler blood flow velocity detection apparatus as claimed in claim 2, further comprising:
    (a) second reference signal generation means for generating a second reference signal of said predetermined frequency fr in response to each of said pulses, said second reference signal having a phase displacement of 90° with said first mentioned reference signal;
    (b) a second multiplier for multiplying an output from said frequency difference signal producing means by said second reference signal; and
    (c) direction detection means for detecting direction of movement of said object such that said output signal of said first multiplier is phase-shifted by 90° of said first reference signal; the phase-shifted signal is added to an output of said second multiplier; and the phase-shifted signal is subtracted from said output of said second multiplier.

4. An ultrasonic Doppler blood flow velocity detection apparatus as claimed in claim 3, further comprising frequency analyzing means for analyzing said signal components from said first and second multipliers in respect to predetermined frequencies.

5. An ultrasonic Doppler blood flow velocity detection apparatus as claimed in claim 4, further comprising correction means for correcting a signal from said detection means such that a square root is calculated from said signal from said detection means.

6. An ultrasonic Doppler blood flow velocity detection apparatus as claimed in claim 4, further comprising a frequency equalizer for equalizing a signal from said detection means having plural bandpass filters for extracting frequency components from said signal from said detection means and plural amplitude correction means for correcting amplitudes of output signals of said plural bandpass filters respectively.

7. An ultrasonic Doppler blood flow velocity detection apparatus as claimed in claim 1, wherein said first and second signal extracting means are bandpass filters and said frequency difference producing means comprises:
    beat signal generation means for producing a beat signal of said output signals of said first and second signal extracting means; and
    beat signal component extracting means for extracting a beat signal component from an output signal of said beat signal generation means.

8. An ultrasonic Doppler blood flow velocity detection apparatus as claimed in claim 7, wherein said beat signal component extracting means comprises multiply means for multiplying said output signal of said first signal extraction means by said output signal of said second signal extracting means and said beat signal component extracting means is a bandpass filter whose center frequency is $|f1-f2|$.

9. A method for detecting blood flow velocity comprising the steps of:
    (a) transmitting ultrasonic waves in response to each pulse of a pulse train and receiving the reflected ultrasonic waves from an ultrasonic-wave reflective object in the blood of a human body and converting the received ultrasonic waves into an electric echo signal;
    (b) extracting a signal component of a first frequency f1 from said echo signal by directly filtering said echo signal;
    (c) extracting a signal component of a second frequency f2 different from said first frequency f1 from said echo signal by directly filtering said echo signal;
    (d) producing a signal having a frequency $|f1-f2|$ using said signal components of said first and second signal extracting steps;
    (e) detecting amplitude of an output signal of said producing step and phase-comparing said output signal with said reference signal; and
    (f) generating a reference signal of a predetermined frequency fr in response to said each pulse, said predetermined frequency fr being approximately equal to the frequency difference $|f1-f2|$.

* * * * *